US005492132A

United States Patent [19]

Weinstein et al.

[11] Patent Number: 5,492,132

[45] Date of Patent: Feb. 20, 1996

[54] APPARATUS TO DELIVER PRESSURE-INDUCED SENSATIONS

[75] Inventors: Sidney Weinstein, Lewisboro, N.Y.; Curt Weinstein, Danbury, Conn.

[73] Assignee: Neurocommunication Research Laboratories, Inc., Danbury, Conn.

[21] Appl. No.: 202,697

[22] Filed: Feb. 25, 1994

Related U.S. Application Data

[63] Continuation of Ser. No. 860,900, Mar. 31, 1992, abandoned.

[51] Int. Cl.[6] .................... A61B 19/00

[52] U.S. Cl. .................... 128/744

[58] Field of Search .................... 128/740, 743, 128/744; 15/207.2; 264/80, 345

[56] References Cited

U.S. PATENT DOCUMENTS

| | | | |
|---|---|---|---|
| 3,633,235 | 1/1972 | Draca | 15/207.2 |
| 3,662,744 | 5/1972 | Low et al. | 128/744 |
| 3,933,148 | 1/1976 | Wyler et al. | 128/744 |
| 4,313,446 | 2/1982 | Kanatani | 128/744 |
| 4,407,302 | 10/1983 | Hirshorn et al. | 128/784 |
| 4,724,569 | 2/1988 | Eguchi et al. | 15/167.1 |
| 4,958,402 | 9/1990 | Weihrauch | 15/207.2 |
| 5,027,828 | 7/1991 | Kovacevic et al. | 128/774 |

OTHER PUBLICATIONS

Article entitled "The repeatability of testing with Semmes–Weinstein Monofilaments", The Journal of Hand Surgery, vol. 12A, No. 1, pp. 155–161, Jan. 1987, by Judith Bell–Krotoski, et al.

Article entitled "Evidence Supporting A New Model For The Evaluation Of Skin Irritation", Journal of Cosmetic Chem., vol. 39 pp. 315–320, Sep./Oct. 1988, by Curt Weinstein, et al.

Article entitled "Somatosensory Changes After Penetrating Brain Wounds In Man", Published by Harvard University Press for The Commonwealth Fund, Cambridge, 1960, title page, and pp. 60–61, by Josephine Semmes, et al.

Article entitled "The Sensational Contributions Of Erik Moberg", The Journal of Hand Surgery, British vol. 15–B, 1990, Pub. by Churchill Livingstone, Edinburgh, title page and pp. 14–24, by A Lee Dellon.

Article entitled "Light Touch–Deep Pressure Testing Using Semmes Weinstein Monolfilaments", Nerve Injuries, 1990, Ed: Hunter etal by Judith A. Bell–Krotoski.

*Primary Examiner*—Stephen C. Pellegrino
*Assistant Examiner*—Guy V. Tucker
*Attorney, Agent, or Firm*—Frishauf, Holtz, Goodman, Langer & Chick

[57] ABSTRACT

An apparatus for measuring skin tactile thresholds and, thus, skin irritation comprises a set of unitarily formed monofilaments whose tips are textured and curved. The unitary tip of the monofilament accordingly does not break or fall off, and due to its texture and curvature is accordingly capable of contacting a skin surface with substantially no slippage for eliciting tactile pressure stimulations that are more consistently of the pressure type than the conventional esthesiometer, which elicits both pressure and pain stimulations randomly. The present apparatus consistently stimulates a skin site with pressure stimuli of various intensities and the perceptual experience of each pressure stimulation can accordingly be accurately recorded in each of two modalities: touch and pain. A method of making the unitarily formed stimulating monofilament comprises providing an elongated monofilament having a tip end portion; applying heat to the tip end portion until the tip end portion balls-up and becomes curved and textured; and mounting a non-free end portion of the monofilament to a handle member.

8 Claims, 6 Drawing Sheets

APPARATUS TO DELIVER PRESSURE-INDUCED SENSATIONS

This application is a Continuation of application Ser. No. 07/860,900, filed Mar. 31, 1992, now abandoned.

BACKGROUND OF THE INVENTION

This invention relates to the measurement of tactile sensation, and more particularly to measurement of both a minimum force to elicit touch sensation and a minimum force to elicit pain sensation in humans, and thus is useful for the measurement of skin irritation in humans.

The present invention is applicable to measuring irritation on various human tissues for example, the oral mucosa, and the like. *Journal of the Society of Cosmetic Chemists*, Volume 39, pages 315–320 describes the effect irritation has on the relationship of the touch and pain thresholds to one another. Other prior art, Semmes, J., Weinstein, S., Ghent, L. and Teuber H. L. (1960) *Somatosensory Changes after Penetrating Brain Wounds in Man*, particularly at page 61, Table B-1, describes the Semmes-Weinstein Pressure Aesthesiometer (trade name used by NCRL (NeuroCommunication Research Laboratories, Inc.), Danbury, Conn.) also generally referred to in the art as Semmes-Weinstein Monofilaments (as sold by North Coast Medical, Inc. of Campbell Calif.). This esthesiometer is a well known device to measure tactile thresholds. It comprises a set of several plastic filaments of constant length with various diameters that result in differing applied maximal forces across the different filaments. An alternative conventional device, e.g., such as the Cochet-Bonet esthesiometer, which is now out of favor, employs a single constant diameter filament which varies in length to control force.

For the purposes of measuring skin irritation according to the model of Weinstein, Drozdenko, and Weinstein (1988), *Journal of the Society of Cosmetic Chemists*, 39, 315–320., for example, it is necessary to measure the thresholds of touch and pain as precisely as possible. In addition, it is necessary to measure the thresholds as rapidly as possible both: (1) to prevent subject fatigue from influencing results, and (2) to obtain a measure of the potentially time-varying level of irritation. Each monofilament is applied to produce a touch or pain sensation depending on the force applied, the subject's threshold and the peculiar characteristics (i.e., whether the tip is flat, sharp or rounded) of each monofilament. The conventional esthesiometer, however, was not reliable, and hence not valid, for producing constant pressure stimulation. That is, the conventional esthesiometer caused pain beyond what would be expected for the applied pressure; this point will be expanded upon below. Moreover, this property of unexpected pain in the prior art is not consistent, but rather is probabilistic, which means that the prior art stimulus characteristics can not reliably form the basis of an evaluative model, such as the aforementioned irritation model.

Specifically, with the conventional esthesiometer device, two types of errors occur during testing on a probabilistic basis due to the characteristics of the apparatus. Of the two aforementioned types of errors, one type of error is filament slippage. The filament may skid across the surface of the skin of the subject instead of contacting and holding to one site. This error is usually obvious to the tester and can be compensated for the most part by restimulating the site as before but without slipping. However, retesting slows the evaluation process and potentially confuses the subject with a different stimulus sensation, that of a monofilament slipping (see FIG. 4). In testing, this type of error occurred for up to about 5% of the stimulations with the conventional device, but not so with the device of the present invention because of its unitary, textured tip (see FIG. 4), as will become apparent from the detailed description hereinbelow.

The second type of error is filament twisting, which is not usually obvious to the tester, and which may occur very frequently. For example, using the prior art device, the full area of the filament tip may not contact the skin being tested, with only a crescent-shaped edge making contact. If only a crescent-shaped portion, rather than the total cross-sectional area, is in effective contact with the skin, then the applied pressure may not be appropriate. What is thus now recognized as a twisting error, was formerly considered by some to be the normal mode of application, which indicates that the twisting-type error is very common. It is apparent that often only the edge of the filament is pressed into the skin. What was previously called a crescent-shaped edge is perhaps better described as the edge of a right cylindrical solid (See FIG. 1A, conventional tip). Filament twisting causes a different face (or a series of different faces, depending upon the degree of twisting) of the stimulation device (monofilament) to be presented (See FIG. 1C, a twisting error, in relation to FIG. 1B, a conventional presentation). Specifically, instead of the flat surface that may be assumed to be stimulating the target site (conventional presentation), the sharp edge of the stimulating device is presented at some unknown and variable angle (a twisting presentation). The result is that the stimulus is more likely to be perceived as painful, rather than as a pressure stimulus (see FIGS. 5 and 6). This second type of error (twisting error) makes the measurement of pain thresholds much less valid, often lowering the actual value that would have occurred. Further, this second type of error also may affect touch thresholds, by changing the nature of the stimulus perceived from merely pressure to sharp pricking, and, hence, pain.

Prior art attempts to alter the contact tip include: (1) a small plastic disk added to the contact tip (FIG. 7A)—attempted around 1955; and (2) a ball-like structure added to the contact tip (FIG. 7B). Adding material to the tip of the filament to standardize the stimulus, however, changes the applied force levels of the low-level force monofilaments. Furthermore, material is not easily added to the tip of a filament, and the added material tends to break or to fall off with repeated stimulations.

The entire contents of all of the publications identified herein and/or listed in the listing of References at the end of this specification are incorporated herein by reference.

The object of the present invention is to solve the above-described problems in the prior art, and specifically to solve the two errors which occur in the prior art devices, by the creation of a stable, functional easy to manufacture tip which better engages the skin of the subject.

SUMMARY OF THE INVENTION

According to the present invention, an apparatus for measuring skin tactile thresholds and, thus, skin irritation comprises a set of unitarily formed monofilaments whose tips are textured and curved. The unitary tip of the monofilament accordingly does not break or fall off, and due to its texture and curvature is accordingly capable of eliciting tactile pressure stimulations that are more consistently of the pressure type than the conventional esthesiometer, which elicits both pressure and pain stimulations randomly. The present invention consistently stimulates a skin site with pressure stimuli of various intensities and the perceptual experience of each pressure stimulation can accordingly be accurately recorded in each of two modalities: touch and pain.

DETAILED DESCRIPTION

The apparatus of the present invention for use in measuring, e.g., skin irritation, will now be described with reference to the figures.

Figure 1A:
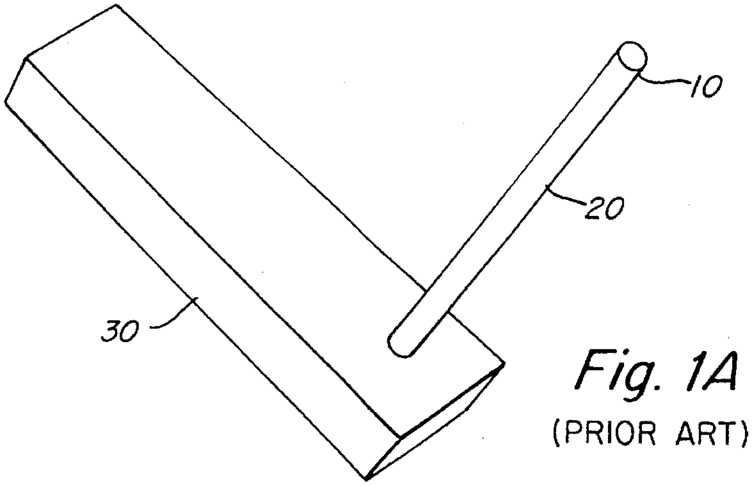
FIG. 1A illustrates the conventional esthesiometer having a conventional stimulation tip.
Figure 1B:
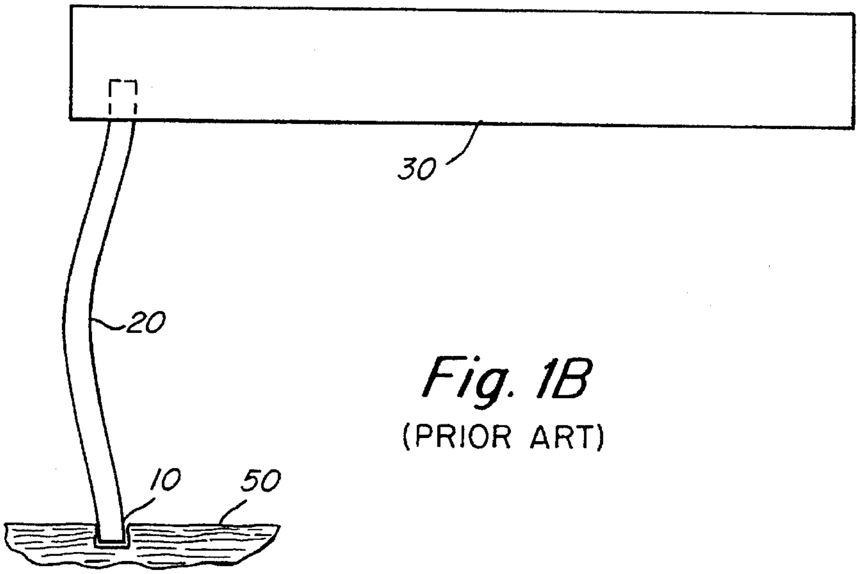
FIG. 1B illustrates the conventional stimulation tip under conventional conditions applying pressure to a subject surface.
Figure 1C:
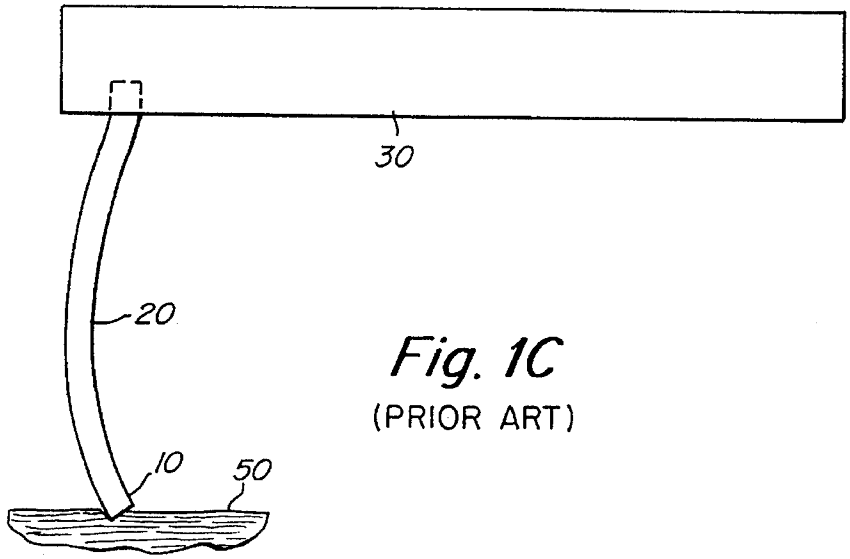
FIG. 1C illustrates the conventional stimulation tip applying pressure to a subject surface with a twisting-error.

FIG. 1A shows a monofilament 20 having a stimulating tip 10 at one end and being connected at its other end substantially perpendicularly to a handle 30, of the conventional Semmes-Weinstein Pressure Aesthesiometer. A set of such objects is conventionally known, each of length about 38 mm and having a different diameter, ranging from 0.0635 mm to 1.143 mm, that conveys a different stimulation force, ranging from 0.0045 gm to 447 gm (see Appendix B, Table B-1, Semmes, Weinstein, et al.). FIG. 1B shows the expected, flat face presentation of the conventional tip 10 to a subject skin surface 50, and FIG. 1C shows the conventional tip 10 during a twisting-error presentation. As shown in FIG. 1C, the face of the conventional tip 10 presented to the subject skin surface 50 is sharp and unpredictably different from the expected-use conditions.

Figure 2A:
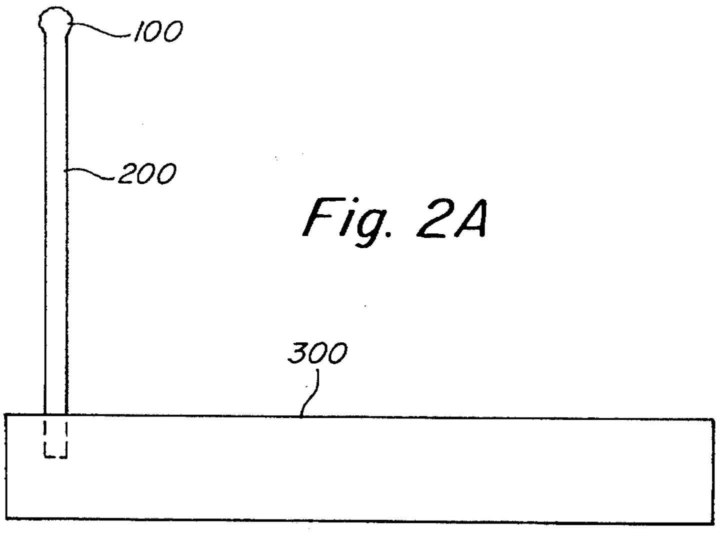
FIG. 2A illustrates the textured, curved stimulation tip of the present invention.
Figure 2B:
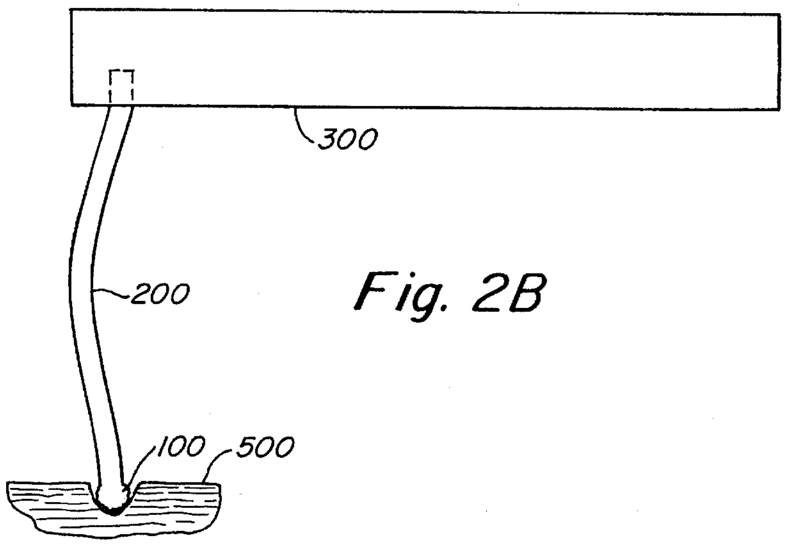
FIG. 2B illustrates the textured, curved stimulation tip of the present invention under expected, usage conditions applying pressure to a subject surface.
Figure 2C:
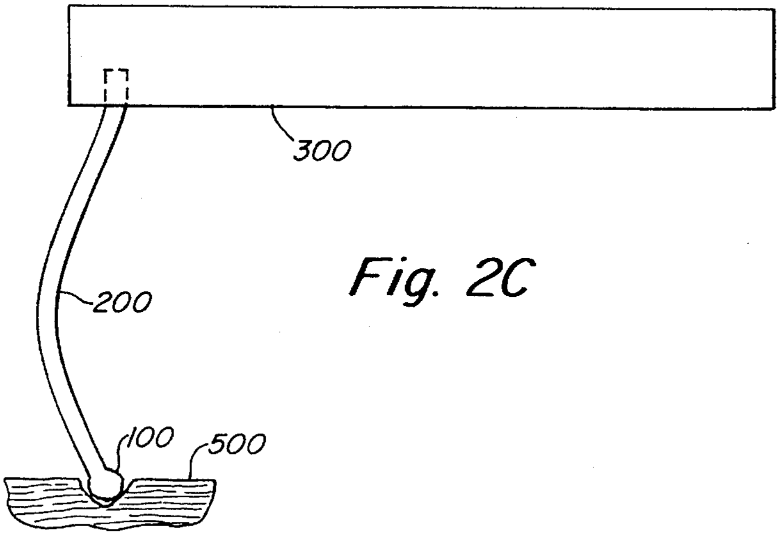
FIG. 2C illustrates the textured, curved stimulation tip of the present invention applying pressure to a subject surface that would cause a twisting error in a conventional tip.

FIG. 2A shows the present invention, which comprises a unitarily formed monofilament 200 having a textured, rounded tip 100 at one end and being connected substantially perpendicularly to a handle 300 at its other end. FIG. 2B presents the invention under expected-use conditions, and FIG. 2C presents the invention under a twisting condition wherein the textured, rounded tip 100 nevertheless presents a face to a subject skin surface 500 that is similar to the expected-use condition.

A distinguishing feature of the present invention is its unitarily formed contacting tip 100. Whereas the conventional monofilament of the Semmes-Weinstein Pressure Aesthesiometer has a tip 10 that closely approximates the end of a right cylinder (see FIG. 1), the monofilament of the present invention has a textured curved tip 100 that is unitarily formed (see FIG. 2) with the elongated body of the monofilament. The advantage of the textured surface is that it makes slippage on the skin surface of the subject less likely (see FIG. 4). The advantage of the curvature is that it functions to negate any twisting errors that occur by presenting essentially the same characteristic contacting face to the skin under conditions when the tip twists and when it doesn't twist. Thus, the stimulus provided by the present invention is more constant (see FIG. 3) and is consistently repeatable with a high degree of accuracy.

Figure 5:
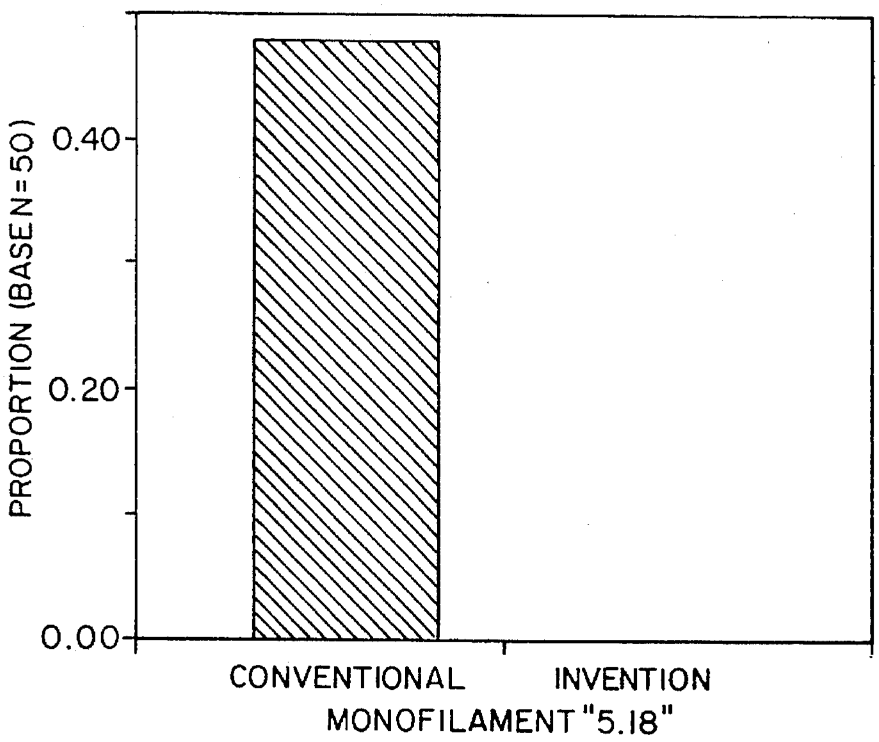
FIG. 5 illustrates the proportions of stimulations perceived as painful for a conventional monofilament and for the monofilament of the present invention, each labeled "5.18" to indicate the force level (the common logarithm of centigrams of average applied force across similar diameter monofilaments).
Figure 6:
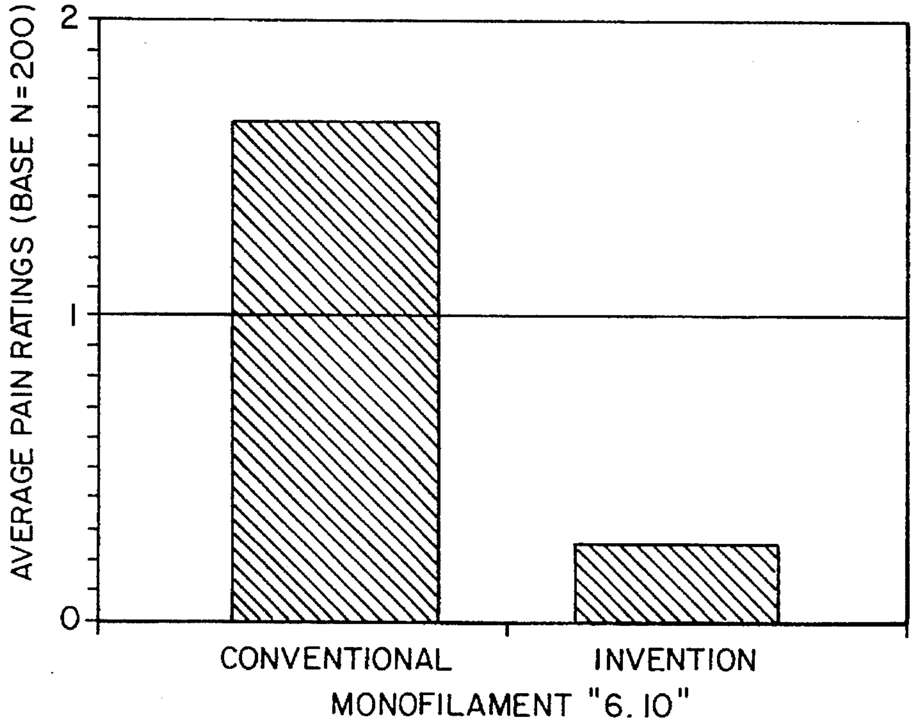
FIG. 6 illustrates the average pain ratings, using a scale of 0 to 10, where 0 is no pain and 10 is a very strong pain, for a same-sized conventional monofilament (labeled "6.10") and monofilament of the present invention.

Accordingly, using the present invention, high level touch stimulations do not appear as if they are pain level stimulations, as would occur in the conventional device if the filament twisted and an edge were presented to the examinee (see FIGS. 5 and 6). Slippage causes an invalid stimulation level to be presented, twisting causes an edge instead of a flat face to be presented, and twisting errors are very common and not easily (if at all) controllable. The enhancement of the tip of the monofilament of the present invention to solve these problems thus achieves great and unexpected advantages over conventional devices and over conventional attempts to attain a consistent stimulus.

Figure 7A:
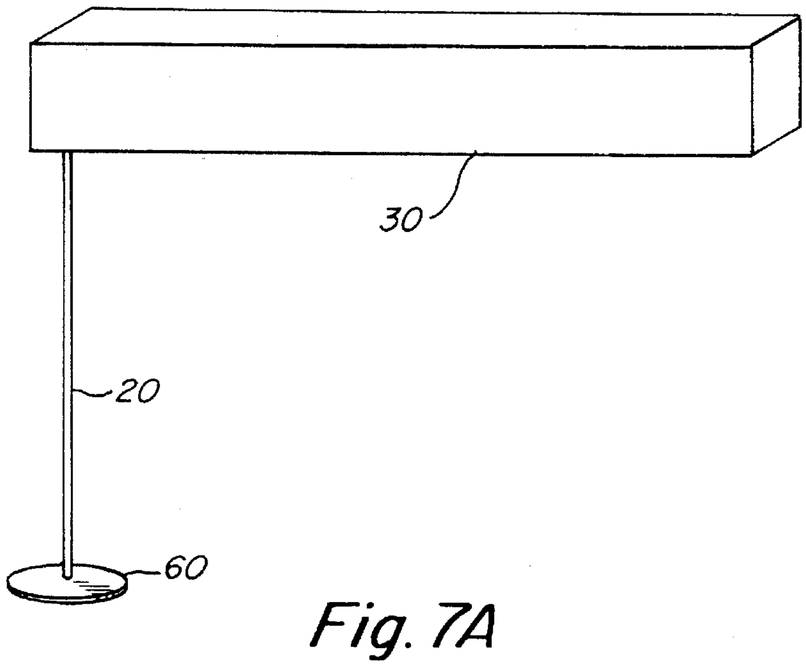
FIG. 7A shows a prior art attempt to attach a plastic disk to the end of a monofilament.
Figure 7B:
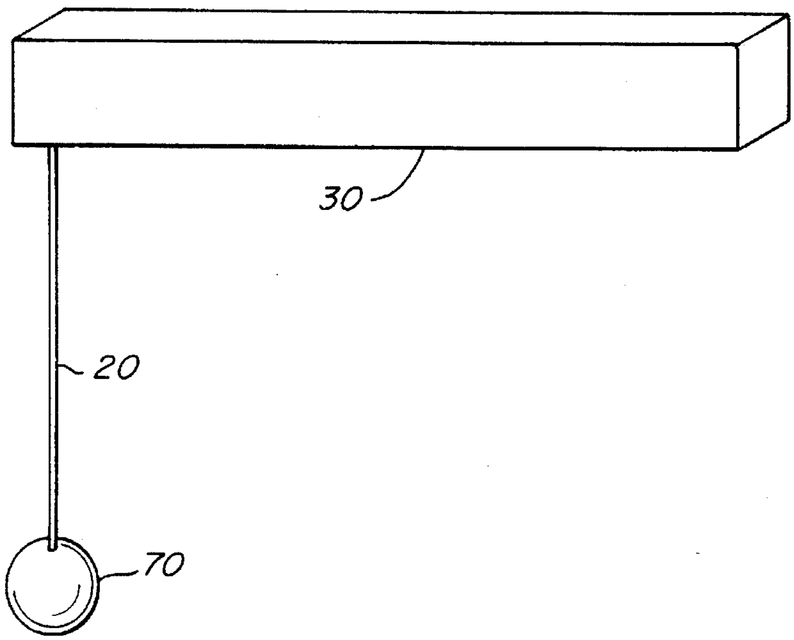
FIG. 7B shows a prior art attempt to attach a spherical-ball-shaped structure to the end of a monofilament.

Previous attempts to attain consistent stimuli have dealt with attaching various structures to the end of the filament, rather than modifying the shape of the filament itself (see FIGS. 7A and 7B). For example, attaching a ball structure 70 to the end of the filament is not practical for small diameter filaments, because of mechanical limitations in attachment, and because the ball structure 70 would add too much weight and change the stimulation characteristics of the monofilament, making the simulation inappropriately large (see FIG. 7B). FIG. 7A shows the addition of a disk structure 60 which creates similar problems.

The method for creating the textured, curved tip of the present invention is to apply heat to the tip of a filament, for example a nylon filament, until melting of the nylon tip causes a bailing-up of the nylon tip to be observed. (Nylon is the generic name for a long-chain of polymeric amid molecules in which recurring amide groups are part of the main polymers chain, and have melting points ranging from about 415° F. to about 480° F.) Heating is ceased after the nylon begins to melt and ball up at the heated tip thereof and further, boils, causing the formation of dimples or craters 400 (see FIG. 8). This procedure causes the tip of the monofilament to become textured, as well as curved, while remaining unitarily formed with the monofilament itself.

More particularly, a nylon monofilament of the Semmes et al. type, for example, such as purchased, for example, from DuPont (Nylon 612), having a free functional length of 38 mm and a diameter (dimension x in FIG. 8) ranging from, for example,0.0635 mm to 1.143 mm, is heated at a temperature of about 415° F. to 500° F., for example by means of a hot plate or other heat source, with the tip of the nylon monofilament spaced from the heat source by a distance, for example, of about ⅛" to ⅜" until balling up (to a diameter y shown in FIG. 8), i.e, melting of the heated tip is observed. The tip is then, for example, air cooled. The length of 38 mm mentioned above is the length extending beyond the part embedded in the handle.

Figure 8:
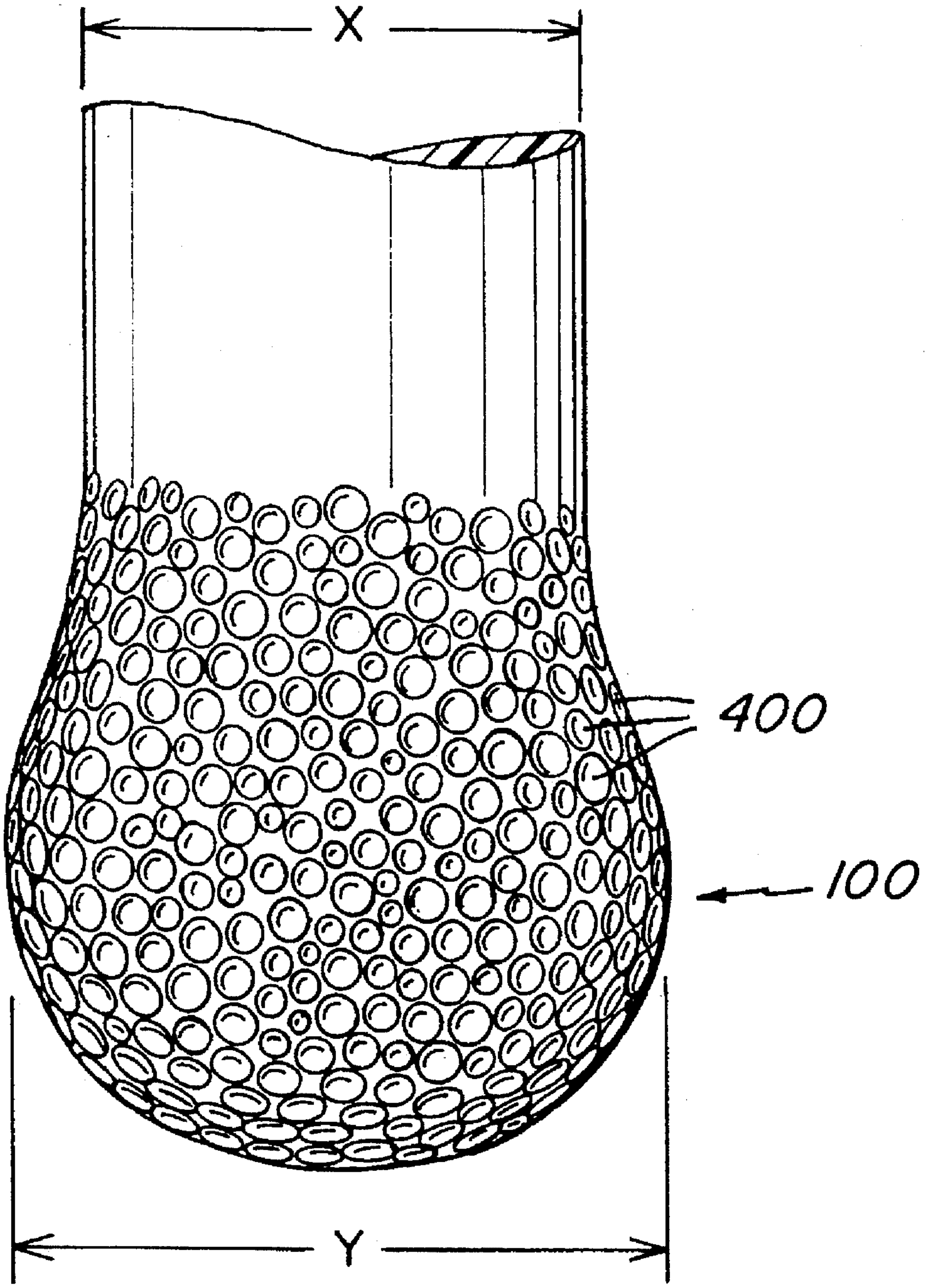
FIG. 8 shows a detailed view of the enhanced, curved and textured stimulating tip of the present invention.

The surface of the tip obtained by this method includes numerous small dimples or craters 400, as shown in FIG. 8 which exhibits the rough surface texture of the tip 100 of the present invention. The diameter of the craters 400 ranges from, for example, 0.0015" to 0.003" and the adjacent craters are distinct from each other. There are, for example, about 200,000 craters per square inch, i.e., with a mean diameter of about 0.00225" yielding a grid of arithmetic-average craters of about 444 by 444 per square inch (i.e, about 444 average craters can be lined up across a distance of one inch) for the monofilament 6.10 of FIGS. 3 and 6. The area of surface contact with the subject skin surface is dependent on the diameter of a particular monofilament, such as the Semmes et al diameters which range from 0.0635 mm to 1.143 mm, with the above described enhancement process of the present invention increasing the diameter at the tip of the particular monofilament by about one third.

The forces applied by the enhanced monofilaments of the present invention are unchanged from the forces applied by the Semmes et al monofilaments of diameters ranging from 0.0635 mm to 1.143 mm, namely the forces applied remain from 0.0045 gm to 447 gm. The difference being, however, that these ideal forces are applied more consistently in pressure by the enhanced monofilament of the present invention. Since the tip of the present invention is wider, the resultant pressure applied by the tip of the present invention is more consistent because the contact face is more consistent both in shape and contact area.

Figure 3:
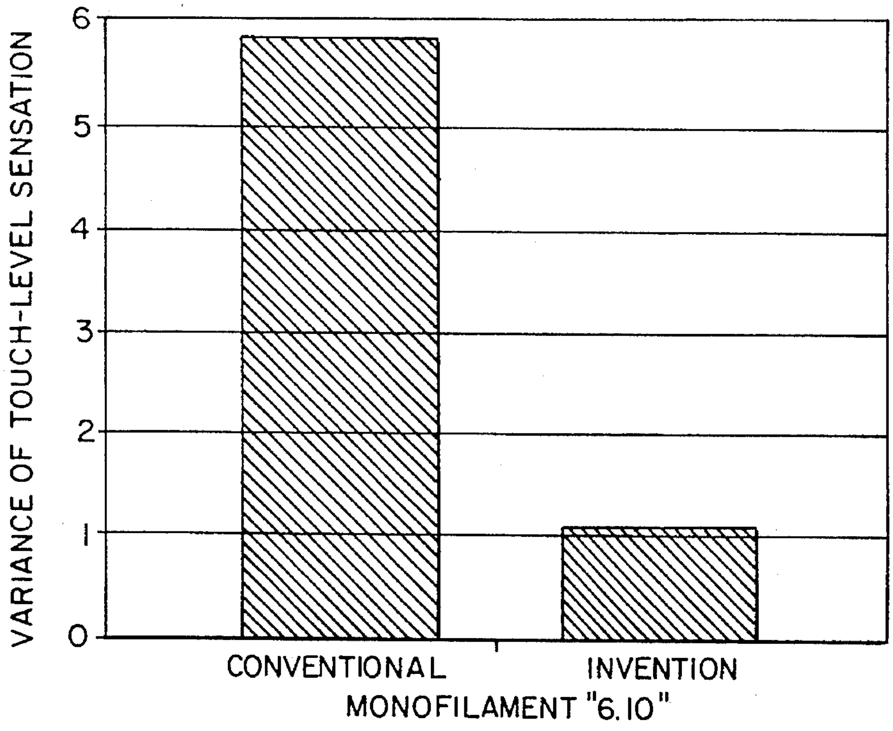
FIG. 3 illustrates the inconsistency of touch-level sensation elicited by the conventional esthesiometer as compared to the present invention.
Figure 4:
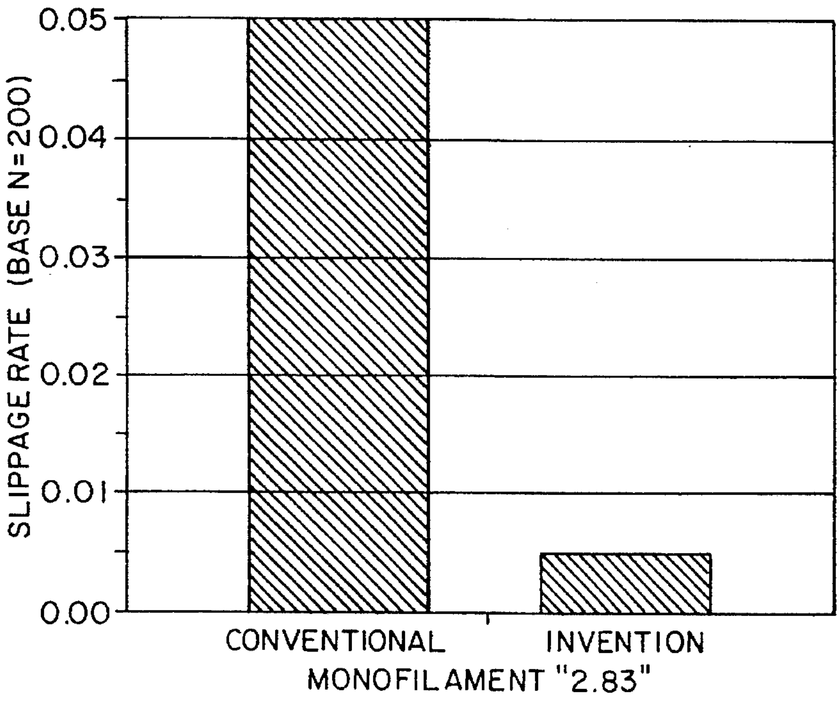
FIG. 4 illustrates high degree of slippage rate of the conventional esthesiometer as compared to the present invention.

The above sizes, dimensions and data concerning the roughening of the surface of the heated tip of the nylon monofilament according to the present invention are observed data for the monofilament 6.10 of FIGS. 3 and 6, and is not limiting of the present inventive concept. The important feature of the present invention is that the heating of the tip end of the monofilament causes balling up or curving of the end surface, while simultaneously causing the creation of a rough or textured surface which contacts the skin, to provide improved results which are discussed further hereinbelow.

An unexpectedly achieved result of the present invention is that pain is not elicited due to twisting errors, but rather due to sufficiently large pressure. This is accomplished by virtue of the curvature of resultant the tip of the monofilament of the present invention. Thus, the differentiation of pain and touch thresholds can be made, which allows, e.g., the irritation model to be accurately applied. As relative sizes in force of the thresholds of touch and pain are used in measuring skin irritation, the device of the present invention thus allows low level (i.e., "subclinical" or "invisible") irritation to be better quantified.

A further unexpectedly achieved result of the present invention is reduction of slippage errors. This is accomplished by the texturing of the tip of the monofilament of the present invention. Though the conventional esthesiometer apparently resists slippage due to its sharp edge, the sharp edge also unintentionally causes pain. The present invention, however, resists slippage even better due to the textured surface of its curved tip, without the negative side effect of pain inducement.

A still further unexpectedly achieved result of the present invention is that the textured, rounded or curved tip of the present invention is unitarily formed with the elongated body or shaft of the monofilament itself and is not achieved by adding a foreign or separate structure to the filament. Attempts at adding a separately formed structure to the monofilaments have been unsuccessful, because the force of stimulation was altered for small-diameter monofilaments and because the added structures tended to break off. In addition to the curvature and texture of the surface which contacts the skin of a subject, the fact that no structure is added to the monofilament of the present invention, and hence that no structure can fall or break off, is yet another advantage of the present invention.

The scope of the present invention is not intended to be limited to the embodiments particularly shown in the drawings and described above in the specification. The present invention is additionally applicable to improving the von-Frey type, single monofilament esthesiometers. It will be obvious to those skilled in the art that various changes may be made without departing from the spirit and scope of the present invention as defined by the following claims.

What is claimed is:

1. An apparatus for delivering pressure-induced sensations to a subject skin surface, said apparatus comprising:

a handle; and an elongated flexible stimulating monofilament made of a heat-meltable nylon material, and which is attached to said handle, said elongated flexible stimulating monofilament having a thin, elongated flexible main portion and a free tip end portion at the very end of said main portion which is most remote from said handle, said monofilament extending a substantial distance from said handle in the direction of the length of said monofilament so as to flex or bend when said free tip end of said monofilament is pressed against a subject skin surface, said free tip end of said monofilament being unitary with said main portion thereof, and said free tip end having a curved stimulating tip surface for contacting the subject skin surface, said curved stimulating tip surface having closely spaced dimples therein over substantially the whole curved tip surface thereof, said dimples forming a rough, uneven textured surface for gripping said subject skin surface so as to reduce slippage of said stimulating tip surface on said subject skin surface upon contacting said subject skin surface and upon application of a force pressing said monofilament against said subject skin surface, Said dimples being spaced apart from each other and having diameters ranging from about 0.0015 inches to 0.003 inches; and said stimulating tip of said stimulating monofilament being curved to a degree such that a similar curved and dimpled surface portion thereof is always presented to said subject skin surface upon contacting said subject skin and upon application of a force thereto to cause said monofilament to flex or bend.

2. An apparatus according to claim 1, wherein said monofilament extends substantially perpendicularly from said handle.

3. An apparatus according to claim 1, wherein said stimulating monofilament comprises a nylon monofilament whose diameter is within a range from about 0.0635 mm to about 1.143 mm.

4. An apparatus according to claim 3, wherein said stimulating tip of said stimulating monofilament has an enlarged diameter which is about one-third larger than said diameter of said stimulating monofilament.

5. An apparatus according to claim 4, wherein said rough uneven surface of said curved stimulating tip comprises about 200,000 dimples per square inch.

6. An apparatus according to claim 5, wherein said dimples have a mean size of about 0.00225".

7. An apparatus according to claim 1, wherein said rough uneven surface of said curved stimulating tip comprises about 200,000 dimples per square inch.

8. An apparatus according to claim 7, wherein said dimples have a mean diameter of about 0.00225".

* * * * *